Figure 4:
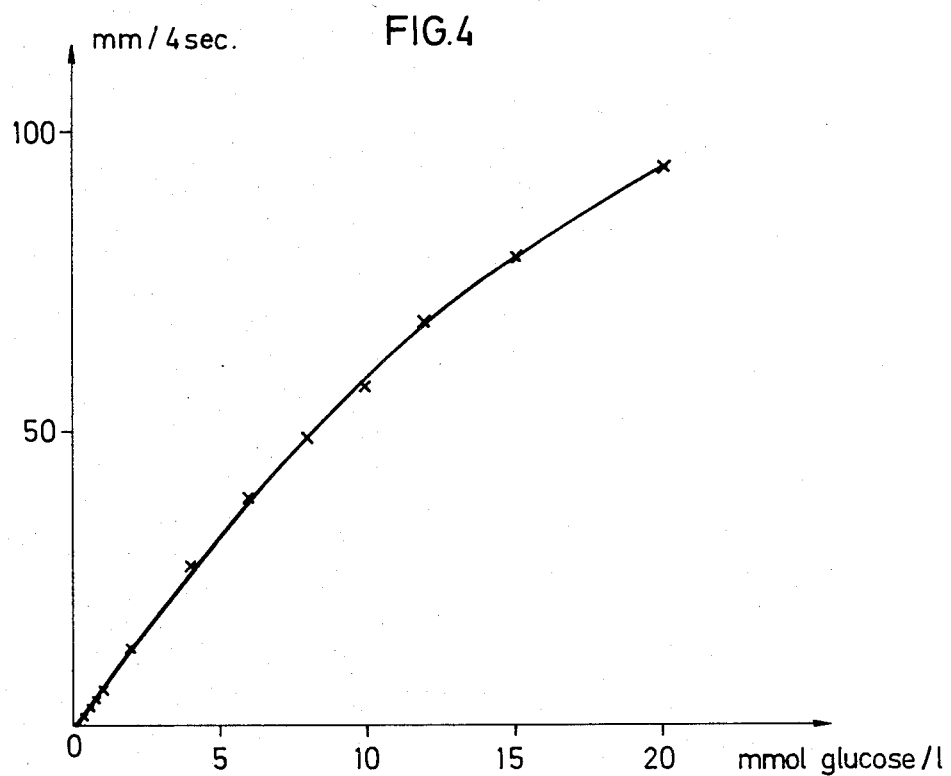

United States Patent [19]

Hansen et al.

[11] 4,399,225
[45] * Aug. 16, 1983

[54] STOP-FLOW ANALYSIS

[75] Inventors: Elo H. Hansen, Lyngby; Jaromir Ruzicka, Holte, both of Denmark

[73] Assignee: Bifok AB, Sollentuna, Sweden

[*] Notice: The portion of the term of this patent subsequent to Feb. 16, 1999, has been disclaimed.

[21] Appl. No.: 296,256

[22] Filed: Aug. 26, 1981

Related U.S. Application Data

[63] Continuation of Ser. No. 48,002, Jun. 13, 1979, abandoned.

[30] Foreign Application Priority Data

Jun. 14, 1978 [SE] Sweden ................................ 7806853

[51] Int. Cl.³ ............................................. G01N 31/14
[52] U.S. Cl. ........................................ 436/34; 436/53
[58] Field of Search ...................... 230/230 R; 435/15; 436/34, 51–53

[56] References Cited

U.S. PATENT DOCUMENTS

| | | | |
|---|---|---|---|
| 3,690,833 | 9/1972 | Ferrari | 23/230 R |
| 3,915,644 | 10/1975 | Walraven | 436/34 |
| 4,022,575 | 5/1977 | Hansen et al. | 23/230 R |
| 4,224,033 | 9/1980 | Hansen et al | 23/230 R |
| 4,315,754 | 2/1982 | Ruzicka et al. | 23/230 R |

OTHER PUBLICATIONS

Hansen et al., "Flow Injection Analysis, etc.," *Analytica Chimica Acta*, 89(1977), pp. 241-254.

*Primary Examiner*—Thomas G. Wyse
*Attorney, Agent, or Firm*—Poms, Smith, Lande & Rose

[57] ABSTRACT

A continuous method of quantitatively determining slowly reacting compounds with the use of a single measuring cell, the sample being injected into a continuously flowing carrier solution which is already provided with, or simultaneously with the sample is provided with reagent to form a sample zone in the form of a reproduceable gradient. Said sample zone is led into a measuring cell whereupon the flow is stopped by means of shunting the carrier flow, by stopping the pump, or by means of a valve. The reaction is allowed to take place in the measuring cell while a magnitude, characteristic for the reaction, is registered. The reaction speed can be detected from the incline of the obtained response curve and the amount of the sought-after compounds is calculated. By means of setting the stop at a certain point in the concentration gradient curve and always selecting said point at the same time distance from the peak of the gradient curve during flow, a total reproduceability of the analysis is ensured.

15 Claims, 5 Drawing Figures

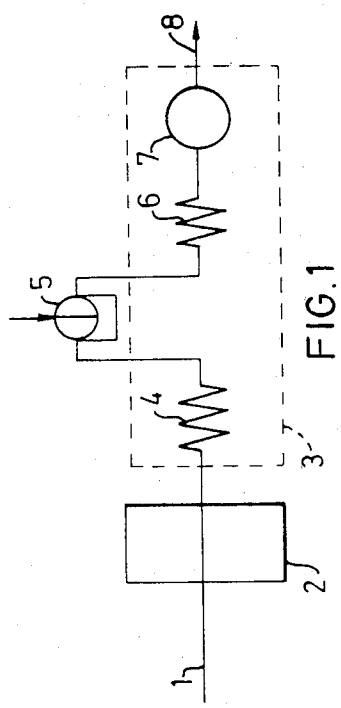
FIG.1
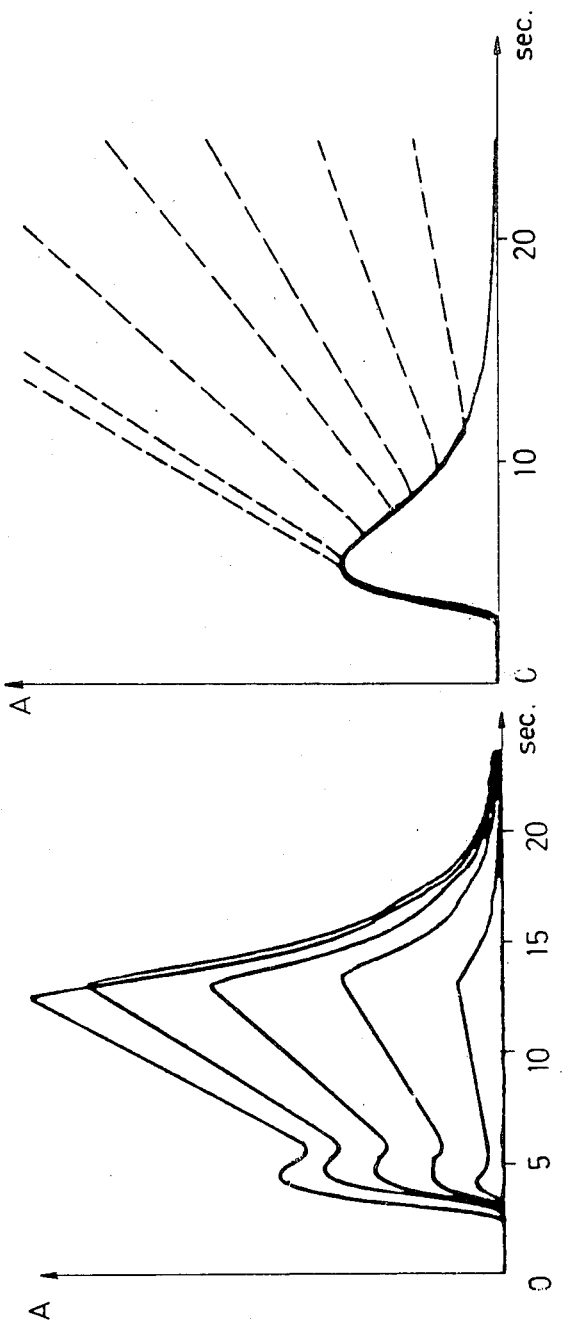
FIG.2
FIG.3

STOP-FLOW ANALYSIS

This is a continuation of application Ser. No. 048,002 filed June 13, 1979, now abandoned.

The present invention is a further development of our original flow injection analysis, that is, analysis with injection of a sample in a continuously flowing continuous carrier solution.

Our continuous analysis method is protected by a number of patents and patent applications in different countries and the principles are described in detail in our previous patent, U.S. Pat. No. 4,022,575.

Flow injection analysis is based on the analysis system being designed so that a reproduceable gradient of the sample is formed in a reagent flow and that measurements of the formed gradient curve, for example spectrophotometric, potentiometric etc. measurements are carried out.

However, in kinetic reactions one can obtain both better selectivity and sensitivity in a sample by studying the reaction speed. Such speed measurements are necessary when enzyme activity and catalytic activity are measured. The basis for our present invention is measurement of the chemical reaction speed. In order to determine the linear part of the reaction response curve so that its derivate or angle, that is, the reaction speed, can be measured with certainty, it is desirable to obtain as many measuring points as possible for each individual analysis. That is difficult to achieve in current continuous flow analysis as the only possible method of analysis has been to place several measuring cells or detectors in succession in the same flow. This is very clumsy and discrete analyses, especially in their most advanced form with centrifugal analysers, have thus a key position for enzyme analyses by means of the signal being able to be detected continuously by these instruments from the moment the reagent and the sample are mixed together.

The purpose of the present invention is to carry out analysis in slow reactions in a simpler and simultaneously considerably more thorough manner.

In the so-called stop-flow method according to the present invention, a single measuring instrument such as a spectrophotometer, a potentiometer etc. is used for detecting the desired magnitude and stops the flow through the measuring cell at a suitable point in time. Thus, the flow can be stopped in various ways; for example, the carrier solution pump can be stopped or the flow can be shut off with a valve arranged before the measuring cell. However, one can also allow the flow to continue without interruption by means of leading it through a shunt conduit past the measuring cell.

By means of its construction, the continuous flow injection analysis allows different means of carrying out the analysis itself. This is something entirely unique for the process.

Firstly, in normal kinetic measurements, two reagent solutions can be led through a mixing chamber so as to obtain a total and immediate mixture of the reaction solutions which each other so that the chemical reaction in the immediately homogenised mixture can begin to be detected within a few milliseconds.

However, such a quick mixture is not desirable in many cases, for example in enzymatic analysis, where a first retarded phase of the magnitude of several seconds often arises. In flow injection analysis, the sample zone, during passage through a tube or coil, is first subjected to a controlled dispersion in the carrier solution which was previously mixed with the reagent (the enzyme solution) and then stops the flow in the measuring cell and detects the chemical reaction continuously on the basis of the reproduceable sample gradient formed in the flow. In many cases, it provides better results to start from the concentration gradients formed during the slow dispersion of the sample zone instead of restricting oneself to measurements of a homogenous solution obtained by means of quick and effective mixture.

Figure 5:
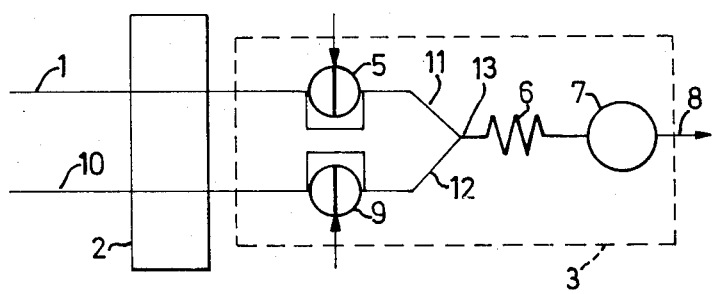

The invention shall be described in more detail below in connection with an embodiment and the accompanying drawings, in which FIG. 1 is an analysis apparatus according to the present invention, FIGS. 2 and 3 are principle reaction curves in the apparatus, FIG. 4 is a calibration curve for practical use, and FIG. 5 is another analysis apparatus according to the present invention.

The specific reaction between glucose dehydrogenase and $\beta$-D glucose is used for the kinetic determination of glucose for investigation and verification of the stop-flow injection principle.

A commerical system glucose enzyme from Merck was used, whereby the co-enzyme nicotinamide-adenin-dinucleotide, NADH, serves as a chromophoric indicator which can be spectrophotometrically measured at 340 nm. Analytical Chimica Acta, 89, (1977), pp. 241–244 presents the background chemistry and reagent compositions and tests with kenetic measurements in one and two points.

The apparatus arrangement in the present tests is shown in FIG. 1. The enzyme and carrier solution is continuously led through a conduit 1 in a continuous flow via a peristaltic pump 2 in an amount of 2.5 ml/min. to a thermostat 3 set at 37° C., where the carrier flow is thermostated in a first coil 4 having a diameter of 0.75 mm and a length of 450 mm in the present case. After said first coil 4, the sample is led to a sample adding apparatus 5, for example of the kind described in detail in our U.S. Pat. No. 4,177,677 issued Dec. 11, 1979, and the mixture of carrier solution, enzyme and sample is allowed to continue through a second coil 6 having a diameter of 0.50 mm and a length of 300 mm to a spectrophotometer 7, where measuring takes place at 340 nm. The solution is led from the spectrophotometer 7 out through the tube 8. As is the case with the coil 4, the coil 6 and the spectrophotometer 7 are situated inside the thermostate 3 which is set at 37° C.

The first test series was made so that the concentration of glucose in the injected sample, 30 microliters, was increased from 1 to 20 millimoles/liter and the sample zone was stopped in the measuring cell as soon as the registered curve reached its maximum. When the flow was interrupted for 9 seconds, a measuring cycle consisting of three parts was obtained; (a) sample injection, dispersion and transportation into the detector, 4.5 seconds, (b) the measuring period with the stopped flow, 9 seconds, (c) the washing period, 10 seconds, after which the next sample was immediately injected. FIG. 2 shows how the sample is added at 0 time, the flow is stopped at 4.5 seconds and started again at 13.5 seconds. This method allows a multi-point, kinetic determination with a speed of 150 samples per hour.

Another aspect of the kinetic analysis according to the invention is shown in FIG. 3 where, in a second test series, the concentration in the injected samples was held constant at 15 mM, but the flow was stopped at different points in time. The dashed curves show how, at a stop, deviation from the solid line measuring curve obtained during continuous flow takes place. By means of the presence of the concentration gradient profiles, different reaction stages between the sample and reagent solution were available for measurement. Thus, the registered response curves obtain different angles and, thus, it is important to always carry out the kinetic measurement in the same section of the sample zone, as was done in the first experiment series. For this type of analysis, the top detector provides a possibility of reproduceably selecting any section of the dispersed sample zone after the maximum peak. Said further flexibility for selection of the ratio sample/reagent provides many interesting aspects for analysis of enzymes.

On the basis of the above-mentioned principle, a number of analyses of glucose have been carried out. A calibration curve was set up on the basis of an arbitrarily selected curve in FIG. 3 with a number of different standard samples. In the calibration curve, the slope is disclosed in mm/4 seconds as a function of mMole glucose. As described above, the measurements were made at a thermostating to 37° C. and with NADH as indicator and measuring at 340 nm.

Analyses were then made of the same samples using a common autoanalyser according to D. Banauch, W. Brümmer, W. Ebeling, H. Metz, H. Rindfrey, H. Lang, K. Leybold and W. Rick, Z. Klin; Chem.Klin.Biochem.,13 (1975) 101, and with our novel method using the calibration curve in FIG. 4.

The following results in mMole glucose/l were obtained:

| Autoanalyser | Stop-flow |
| --- | --- |
| 5.3 | 5.6 |
| 8.6 | 9.5 |
| 4.7 | 4.9 |
| 6.5 | 6.4 |

As can be seen in the table, the use of the present invention provides results corresponding well with previous methods, but in a much quicker and simpler manner.

As the enzyme or substrate solution is often very expensive, it is economically advantageous not always to be forced to pump it through the analysis apparatus as it only needs to be present in that part of the flow containing the sample zone. This demand is met by an apparatus of the kind shown in FIG. 5, where two exactly synchronized injection valves are used, one having 10 microliters volume for sample injection and the other 9 having a 30 microliter volume for injection of the enzyme reagent. The carrier flow consisted of distilled water. The conduits 11 and 12 were carefully adapted, each having a length of 10 mm and an inner diameter of 0.5 mm, in order to provide an exact synchronisation of the sample zone and the reagent zone at meeting point 13. The other reference numerals in FIG. 5 have the same meanings as corresponding reference numerals in FIG. 1.

As in FIG. 1, FIG. 5 shows thermostating of the flows between the peristaltic pump 2 and the sample addition valves. In the latter embodiment according to FIG. 5, however, said thermostating prior to addition can be avoided as no reaction takes place until after the meeting point 13, and the conduits 11 and 12 suffice to ensure a temperature equilibrium before the reaction takes place after the meeting point 13.

The determination of glucose with the use of glucose hydrogenase as enzyme, based on the previously disclosed chemistry, provided results identical to results obtained when the carrier flow always consisted of glucose hydrogenase in the phosphate buffer, FIGS. 1–4. Even if the enzyme reagent solution must be more concentrated in reaction injection than in the continuously flowing reaction solution when the reaction zone is dispersed, a considerable savings of the enzyme reagent is obtained. When the pumping time in the first test was a total of 15 seconds and the pumping speed was 2.5 ml/minute, corresponding to 0.6 ml, 1.4 kU/l, only 0.03 ml enzyme was consumed per analysis in the second test, 7.04 kU/l glucose hydrogenase, that is, enzyme production was reduced to a fourth. By means of water being used as carrier solution, washing of the apparati between different analyses is avoided. In any case, washing is reduced to a minimum.

What we claim is:

1. A method for determining the reaction speed of a sample at selected sample concentrations within a sample mixture slug comprising the steps of:
   introducing a sample into a flowing carrier stream to form a sample mixture slug having a forward head portion, a rearward tail portion and a central portion, said sample dispersing within said sample mixture slug to form reproduceable concentration gradients in said head and tail portions in which the concentration of said sample varies;
   flowing said carrier stream and sample mixture slug through a measuring cell without removing the head portion or tail portion from said sample mixture slug;
   stopping the flow of said carrier stream in response to a selected concentration of sample within one of said concentration gradients as said sample mixture slug passes through said measuring cell; and
   measuring the reaction of said sample at said selected concentration for a period of time whereby said reaction speed of said sample at said selected sample concentration may be determined.

2. A method according to claim 1 wherein one or more reagents are introduced into said carrier stream to form a reagent carrier stream having reagent uniformly dispersed therein for reaction with sample.

3. A method according to claim 2 wherein said selected sample concentration is determined by measuring a reaction product of said sample and said reagent.

4. A method according to claim 3 wherein samples are sequentially introduced into said flowing carrier stream.

5. A method according to claim 3 wherein said sample concentrations are selected by varying the time period between introduction of said sample into said carrier stream and stopping said carrier stream flow.

6. A method according to claim 2 wherein said reagent is introduced into said carrier stream after said sample is introduced therein.

7. A method according to claim 2 or 6 where said reagent is introduced noncontinuously into said carrier stream as a discrete reagent slug in such a manner to provide mixing of said sample mixing slug and said regent slug in said carrier stream.

8. A method according to claim 1 where the concentration of sample in said concentration gradients increases inward towards the central portion of said sample mixture slug.

9. A method according to claim 8 where the section of said sample mixture zone measured within said measuring cell is selected from the forward or rearward ends of said concentration gradient and not from said central portion.

10. A method according to claim 1 wherein reaction speeds at different sample concentrations within said sample zone are measured by changing the time period between introduction of said sample into said carrier stream and stopping said carrier stream flow.

11. In a method of analysis where a sample is introduced into a flowing carrier stream to form a sample mixture slug having a forward head portion, a rearward tail portion and a central portion, said sample dispersing to form reproducable concentration gradients in said head and tail portions in which the concentration of said sample varies, said sample undergoing a reaction while in said carrier stream, wherein the improvement comprises measuring the reaction speed of said sample at one or more selected sample concentrations within said concentration gradients by stopping the flow of said carrier stream and measuring the reaction of said sample at said selected sample concentrations for a period of time.

12. A method according to claim 11 in which measureable reaction products are produced by said sample reaction, said reaction product formation being related to said sample concentration, wherein said selected sample concentrations are determined indirectly by measurement of said reaction product formation.

13. A method of determining the change in a changing characteristic of a sample at selected sample concentrations comprising the steps of:
    introducing a sample into a flowing carrier stream to form a sample mixture slug having a forward head portion, a rearward tail portion and a central portion, said sample dispersing within said sample mixture slug to form reproduceable concentration gradients in said head and tail portions in which the concentration of said sample varies, said sample having a measureable changing characteristic;
    flowing said carrier stream and sample mixture slug through a measuring cell without removing the head or tail portion from said sample mixture slug;
    stopping the flow of said carrier stream in response to a selected concentration of sample within one of said concentration gradients as said sample mixture slug passes through said measuring cell; and
    measuring the changing characteristic of said sample at said selected concentration for a period of time whereby the change in said characteristic of said sample at said selected concentration may be determined.

14. A method according to claim 13 wherein said changing characteristic is a reaction between said sample and one or more reagents added to said sample.

15. A method according to claim 14 wherein said reaction produces a measurable reaction product, said selected sample concentration being determined by measuring said reaction product.

* * * * *